(12) United States Patent
Lao et al.

(10) Patent No.: US 8,741,569 B2
(45) Date of Patent: Jun. 3, 2014

(54) METHODS FOR NORMALIZING AND FOR IDENTIFYING SMALL NUCLEIC ACIDS

(75) Inventors: Kai Lao, Pleasanton, CA (US); Neil Straus, Emeryville, CA (US); John Burns, Carlsbad, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 746 days.

(21) Appl. No.: 12/604,792

(22) Filed: Oct. 23, 2009

(65) Prior Publication Data
US 2010/0112581 A1   May 6, 2010

Related U.S. Application Data

(63) Continuation of application No. 11/093,587, filed on Mar. 29, 2005, now abandoned.

(51) Int. Cl.
*C12Q 1/68* (2006.01)
*C07H 21/04* (2006.01)

(52) U.S. Cl.
USPC .......................................... 435/6.12; 536/24.2

(58) Field of Classification Search
None
See application file for complete search history.

(56) References Cited

U.S. PATENT DOCUMENTS 6,007,983 A * 12/1999 Dunn et al. .................... 435/5
6,017,702 A    1/2000 Lee et al.
2002/0197616 A1 12/2002 Nunez et al.
2003/0113781 A1  6/2003 Bortolin et al.
2003/0207279 A1 11/2003 Crothers et al.

FOREIGN PATENT DOCUMENTS

| EP | 534858 A1 | 3/1993 |
| WO | WO 02061140 A2 | 8/2002 |
| WO | WO 03/029459 A2 | 4/2003 |
| WO | WO03029459 | 4/2003 |

OTHER PUBLICATIONS

International Search Report for application No. PCT/US2006/012025, Mail date Oct. 16, 2007, 1 page.
Lagos-Quintana et al Supplementary Material (online) available Apr. 30, 2002 (retrieved on Apr. 24, 2009) retrieved from http://www.cell.com/current-biology/supplemental/S0960-9822(02)00809-6 (15 pages).
Lagos-Quintana et al. Identification of tissue-specific microRNAs from mouse. Current Biology 12(9):735-739, Apr. 30, 2002.
Juarez et al. microRNA-mediated repression of rolled leaf1 specifies maize leaf polarity. Nature 428:84-88, Mar. 4, 2004.

(Continued)

*Primary Examiner* — Samuel Woolwine (57) ABSTRACT

The present teachings are generally directed to methods for normalizing at least one species of small nucleic acid that is present in a population of small nucleic acid species, wherein the relative concentration of at least one small nucleic acid species is substantially greater than the relative concentration of at least one other small nucleic acid species in the population. At least one small nucleic acid species is normalized using a multiplicity of primers comprising degenerate sequences. In some embodiments, a small nucleic acid species is identified by inserting at least part of an extension product from a normalized population into a vector and subsequently sequencing the insert. In some embodiments, a small nucleic acid species is identified by determining the sequence of at least part of an extension product.

18 Claims, 2 Drawing Sheets

(56) References Cited

OTHER PUBLICATIONS

Brennecke et al, "Towards a complete description of the microRNA complement of animal genomes", Genome Biology, Aug. 21, 2003, vol. 4, issue 9, pp. 228.1-228.3.

Elbashir et al. RNA interference is medicated by 21- and 22-nucleotide RNAs. Genes & Development, 2001, vol. 15, pp. 188-200.

U.S. Appl. No. 11/093,587, filed Mar. 29, 2005.

* cited by examiner

METHODS FOR NORMALIZING AND FOR IDENTIFYING SMALL NUCLEIC ACIDS

This application is a continuation of U.S. application Ser. No. 11/093,587, filed Mar. 29, 2005, which is incorporated herein by reference.

FIELD

The present teachings relate generally to the fields of biotechnology and molecular biology. More specifically, the present teachings relate to methods for normalizing populations of small nucleic acids and for identifying species of small nucleic acids within such normalized populations.

INTRODUCTION

The recent discovery that small nucleic acid molecules play a role in cell regulation, including without limitation gene silencing and translational repression, has lead to a great interest in identifying and analyzing these molecules. Small RNA molecules, for example but not limited to small interfering RNA (siRNA) and microRNA (miRNA), have been implicated in gene regulation, chromatin condensation, antiviral defense, suppression of transposon hopping, and genomic rearrangement. Many of these small nucleic acid species were first identified by cloning size fractionated populations of polynucleotides (see, e.g., Elbashir et al., Genes & Development 15:188-200, 2001; Lau et al., Science 294:858-62, 2001; Ambros et al., Curr. Biol. 13:807-18, 2003; Lim et al., Genes & Development 17:991-1008, 2003; Lai et al., Genome Biol. 4:R42, 2003; and Suh et al., Develop. Biol. 270:488-98, 2004). However, it is believed that some small nucleic acid species may be difficult to isolate because of their low abundance or cloning biases inherent in conventional cloning procedures, including without limitation the overabundance of certain clones relative to other clones (see, e.g., Lim et al., Genes & Development 17:991-1008, 2003; and Ambros et al., Curr. Biol. 13:807-18, 2003). It has also been suggested that, at least for miRNA, we have reached the identification limit of conventional isolation and cloning methods (see, e.g., Lagos-Quintana et al., RNA 9:175-79, 2003; and Lai et al., Genome Biol. 4:R42, 2003). Novel cloning and identification methods would, among other things, further our knowledge of small nucleic acid species and their role in developmental biology and disease.

SUMMARY

The present teachings are directed to methods, reagents, and kits for normalizing a population of different small nucleic acid species of varying abundance, e.g., a population comprising at least one species of small nucleic acid with a relative concentration that is substantially less than at least one other small nucleic acid species in the population. Also disclosed are methods for identifying at least one species of small nucleic acid in the normalized population.

Some disclosed methods for normalizing a population of different small nucleic acid species of varying abundance comprise ligating adapters to one or both ends of at least some of the small nucleic acids to form a multiplicity of adapter-modified molecules, and amplifying the multiplicity of adapter-modified molecules with a multiplicity of primers to generate extension products. At least some of the primers comprise (a) a degenerate sequence at their 3'-end and (b) a portion that is complementary to or is the same as a region of an adapter-modified molecule, an extension product, or both.

By amplifying the population of adapter-modified molecules using appropriate concentrations of forward and reverse primers, at least some of which comprise degenerate sequences, a normalized population can be generated. In some embodiments, populations of normalized small nucleic acid species are generated by (1) ligating 3' adapters and/or 5' adapters with small nucleic acids using a ligase, typically an RNA ligase, followed by (2) RT-PCR using (a) formulated relative concentrations of (i) forward primers and (ii) reverse primers, and (b) strategic primer sequence design, including the use of different degenerate sequences.

According to certain methods, the nucleotide sequence of at least part of a normalized nucleic acid is determined and the corresponding small nucleic acid species is identified. In some embodiments, at least part of a normalized nucleic acid is determined using a sequencing technique and the corresponding small nucleic acid species is identified. In some embodiments, at least a portion of a normalized nucleic acid is inserted into a recombinant vector. The vector comprising the insert is transferred to an appropriate host cell and amplified in vivo. At least a part of the amplified insert is determined using a sequencing technique and the corresponding nucleic acid species is identified.

These and other features of the present teachings are set forth herein.

DRAWINGS

The skilled artisan will understand that the drawings, described below, are for illustration purposes only and are not intended to limit the scope of the present teachings in any way.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a primer" means that more than one primer can be present, including without limitation, one or more copies of a particular primer species, as well as one or more different species of a particular primer type, including without limitation two different species of first reverse primers. Also, the use of "comprise", "comprises", "comprising", "contain", "contains", "containing", "include", "includes", and "including" are not intended to be limiting. The term and/or means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. In the event that one or more of the incorporated literature and similar materials contradicts this application, including but not limited to defined terms, term usage, described techniques, or the like, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

I. Some Definitions

An "adapter-modified molecule" results from the ligation of at least one adapter to a small nucleic acid by a ligation agent. In some embodiments, a "double adapter-modified molecule" is generated when a 5' adapter is ligated to the 5'-end of a small nucleic acid and a 3' adapter is ligated to the 3'-end of the same small nucleic acid (see, e.g., panel A of FIG. 1). In some embodiments, a "single adapter-modified molecule" is generated when one adapter is ligated to the appropriate end of a small nucleic acid (see, e.g., FIG. 2). In some embodiments a multiplicity of 5' adapters and a multiplicity of 3' adapters are combined with a multiplicity of different small nucleic acids and a ligation agent and, under appropriate conditions, a multiplicity of different adapter-modified molecules are generated, which can include both single adapter-modified molecules and double adapter-modified molecules. Adapter-modified molecules serve as templates for generating first extension products, which in turn can serve as templates for generating second extension products, and so forth.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "corresponding" as used herein refers to at least one specific relationship between the elements to which the term relates. For example, a first reverse primer corresponds to an adapter-modified molecule, a first extension product corresponds to an adapter-modified molecule, a first forward primer corresponds to a first extension product, and so forth. Additionally, a third extension product species can serve as a surrogate for the corresponding second extension product species, a second extension product species can serve as a surrogate for the corresponding first extension product species, which can serve as a surrogate for the corresponding adapter-modified molecule species or at least part of an adapter-modified molecule, which can serve as a surrogate for the corresponding small nucleic acid species, and so forth.

The term "extending enzyme" refers to a polypeptide that is able to catalyze the 5'-3'extension of a hybridized primer in a template-dependent manner under suitable reaction conditions including without limitation, appropriate nucleotide triphosphates, cofactors, buffer, and the like. Extending enzymes are typically DNA polymerases or RNA polymerases, for example but not limited to, RNA-dependent DNA polymerases, including without limitation reverse transcriptases, and DNA-dependent DNA polymerases, including without limitation DNA polymerases that, at least under certain conditions, share properties of both of these classes of DNA polymerases, and RNA-dependent RNA polymerases. In certain embodiments, an extending enzyme is a reverse transcriptase, for example but not limited to, retroviral reverse transcriptases such as Avian Myeloblastosis Virus (AMV) reverse transcriptase and Moloney Murine Leukemia Virus (MMLV) reverse transcriptase. In certain embodiments, an extending enzyme is a DNA-dependent DNA polymerase, including without limitation Taq DNA polymerase and the Klenow fragment of DNA polymerase I. Certain DNA-dependent DNA polymerases possess reverse transcriptase activity under some conditions, for example but not limited to, the DNA polymerase of *Thermus thermophilus* (Tth DNA polymerase, E.C. 2.7.7.7) which demonstrates reverse transcription in the presence of $Mn^{2+}$, but not $Mg^{2+}$ (see also, GeneAmp® AccuRT RNA PCR Kit and Hot Start RNA PCR Kit comprising a recombinant polymerase derived from *Thermus* species Z05, both from Applied Biosystems). Likewise, certain reverse transcriptases possess DNA polymerase activity under certain reaction conditions, including without limitation, AMV reverse transcriptase and MMLV reverse transcriptase. In some embodiments, an extending enzyme is a RNA polymerase, including without limitation T3, SP6, and T7 bacteriophage RNA polymerases. Descriptions of extending enzymes can be found in, among other places, Lehninger Principles of Biochemistry, 3d ed., Nelson and Cox, Worth Publishing, New York, N.Y., 2000 ("Lehninger"), particularly Chapters 26 and 29; Twyman, Advanced Molecular Biology: A Concise Reference, Bios Scientific Publishers, New York, N.Y., 1999; Ausubel et al., Current Protocols in Molecular Biology, John Wiley & Sons, Inc., including supplements through February 2005 ("Ausubel et al."); and Enzymatic Resource Guide: Polymerases, Promega, Madison, Wis., 1998. Expressly within the intended scope of the term extending enzyme are enzymatically active mutants or variants thereof, as are enzymes modified to confer different temperature-sensitive properties (see, e.g., U.S. Pat. Nos. 5,773,258; 5,677,152; and 6,183,998; and DNA Amplification: Current Techniques and Applications, Demidov and Broude, eds., Horizon Bioscience, 2004, particularly in Chapter 1.1).

The term "formulated relative concentration" refers to (i) the quantity of at least one primer comprising a degenerate sequence compared with the quantity of the corresponding adapter-modified molecules or (ii) the quantity of a degenerate primer compared with the quantity of the corresponding primer of a primer pair, wherein the number of degenerate primer molecules is less than the number of corresponding adapter-modified molecules or the number of the corresponding primers of the primer pair, respectively. For illustration purposes but not as a limitation, a primer pair comprising a multiplicity of different first reverse primers, each comprising a different degenerate sequence and a universal forward primer, wherein the multiplicity of different first reverse primers are present in limiting concentration and the universal forward primer is present in excess. In some embodiments, each of the degenerate primer species is present in equimolar or at least relatively similar concentration compared to the other degenerate primer species, and the collective concentration of the multiplicity of degenerate primer species is limiting with respect to the concentration of the corresponding primer of the primer pair. In some embodiments, a universal primer is used with a multiplicity of corresponding primer species comprising different degenerate sequences and the concentration of the universal primer species is at least 3 times, at least 5 times, or at least 10 times the concentration of any of the individual primer species comprising degenerate sequences and the concentration of the universal primer species is greater than the total concentration of all of the corresponding primer species comprising degenerate sequences. Those in the art will appreciate that with appropriate design, a formulated relative concentration of primers can be used according to the present teaching for generating a normalized population.

The terms "hybridizing" and "annealing", including without limitation variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portion of the primers and their corresponding binding sites in adapter-modified molecules and/or extension products, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of the primers, adapter-modified molecules, and/or extension products can also influence hybridization conditions. Thus, the preferred annealing conditions will depend upon the particular application. Such conditions, however, can be routinely determined by persons of ordinary skill in the art, without undue experimentation. Typically, annealing conditions are selected to allow the disclosed primers to selectively hybridize with a complementary or substantially complementary sequence in their corresponding adapter-modified molecule and/or extension product, but not hybridize to any significant degree to other sequences in the reaction.

The term "ligation agent" as used herein comprises any enzymatic or non-enzymatic reagent that can effect ligation of nucleic acids to one another, including without limitation, ligases, chemical ligation agents, and photoligation. For example, ligase is an enzymatic ligation agent that, under appropriate conditions, forms phosphodiester bonds between the 3'-OH and the 5'-phosphate of adjacent nucleic acid sequences, including without limitation between an adapter and a small nucleic acid, provided that they are both suitable for ligation together.

Chemical ligation agents include without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the present teachings. Protocols for chemical ligation methods and descriptions of appropriate reactive groups can be found in, among other places, Xu et al., Nucl. Acids Res., 27:875-81, 1999; Gryaznov and Letsinger, Nucl. Acids Res. 21:1403-08, 1993; Gryaznov et al., Nucleic Acid Res. 22:2366-69, 1994; Kanaya and Yanagawa, Biochemistry 25:7423-30, 1986; Luebke and Dervan, Nucl. Acids Res. 20:3005-09, 1992; Sievers and von Kiedrowski, Nature 369:221-24, 1994; Liu and Taylor, Nucl. Acids Res. 26:3300-04, 1999; Wang and Kool, Nucl. Acids Res. 22:2326-33, 1994; Purmal et al., Nucl. Acids Res. 20:3713-19, 1992; Ashley and Kushlan, Biochemistry 30:2927-33, 1991; Chu and Orgel, Nucl. Acids Res. 16:3671-91, 1988; Sokolova et al., FEBS Letters 232:153-55, 1988; Naylor and Gilham, Biochemistry 5:2722-28, 1966; James and Ellington, Chem. & Biol. 4:595-605, 1997; and U.S. Pat. No. 5,476,930.

Photoligation using light of an appropriate wavelength as a ligation agent is also within the scope of the current teachings. In certain embodiments, photoligation comprises adapters comprising nucleotide analogs, including but not limited to, 4-thiothymidine ($s^4T$), 5-vinyluracil and its derivatives, or combinations thereof. In certain embodiments, the ligation agent comprises: (a) light in the UV-A range (about 320 nm to about 400 nm), the UV-B range (about 290 nm to about 320 nm), or combinations thereof, (b) light with a wavelength between about 300 nm and about 375 nm, (c) light with a wavelength of about 360 nm to about 370 nm; (d) light with a wavelength of about 364 nm to about 368 nm, or (e) light with a wavelength of about 366 nm. In certain embodiments, photoligation is reversible. Descriptions of photoligation can be found in, among other places, Fujimoto et al., Nucl. Acid Symp. Ser. 42:39-40, 1999; Fujimoto et al., Nucl. Acid Res. Suppl. 1:185-86, 2001; Fujimoto et al., Nucl. Acid Suppl., 2:155-56, 2002; Liu and Taylor, Nucl. Acid Res. 26:3300-04, 1998; and on the world wide web at: sbchem.kyoto-u.ac.jp/saito-lab.

When used in the context of the current teachings, the term "suitable for ligation" refers to one or more ends of a nucleic acid molecule, including without limitation an adapter and a small nucleic acid, comprising an appropriately reactive group for a particular ligation agent. For example but not limited to, the 3'- and 5'-ends of a small nucleic acid, the 5'-end of a 3' adapter, and the 3'-end of a 5' adapter. Exemplary pairs of reactive groups include, but are not limited to: a nucleotide 3'-hydroxyl group on the 3' end of a 5' adapter and a nucleotide 5'-phosphate group on the 5' end of a small nucleic acid; phosphorothioate and tosylate or iodide; esters and hydrazide; $RC(O)S^-$, haloalkyl, or $RCH_2S$ and $\alpha$-haloacyl; thiophosphoryl and bromoacetoamido groups.

A "population of different small nucleic acid species" is the group or set of nucleic acids obtained from a sample, typically a size fractionated sample, that contains or may contain small nucleic acids of interest. Typically the different small nucleic acid species in the population are present in varying concentrations, i.e., the relative amount of at least one small nucleic acid species in the sample is different from, for example substantially less than, the relative amount of at least one other small nucleic acid species in that population. A normalized population comprises the group of different nucleic acid sequences, e.g., extension products, generated by a normalizing step of the current teachings, wherein the relative concentration of at least two different small nucleic acid species are brought closer to equivalency, as measured by the relative concentrations of their corresponding extension products generated during the normalizing.

As used herein, the term "primer-binding site" refers to a region of a polynucleotide sequence that can serve directly, or by virtue of its complement, as the template upon which a primer can anneal for any of a variety of primer extension reactions known in the art (for example, PCR). It will be appreciated by those of skill in the art that when two primer-binding sites are present on a single polynucleotide (for example but not limited to a first extension product or a second extension product), the orientation of the two primer-binding sites is generally different. For example, one primer of a primer pair is complementary to and can hybridize with the first primer-binding site, while the corresponding primer of the primer pair can hybridize to the complement of the second primer-binding site. Stated another way, in some embodiments, the first primer-binding site can be in a sense orientation, and the second primer-binding site can be in an antisense orientation. In addition, "universal" primers and primer-binding sites as used herein are generally chosen to be as unique as possible given the particular assays and host genomes to ensure specificity. In some embodiments, at least one of the primer-binding sites comprise a promoter sequence, including without limitation a sequence suitable for binding T3 RNA polymerase, T7 RNA polymerase, or SP6 RNA polymerase.

A "small nucleic acid" as that term is used herein, refers to a polynucleotide species that is present in a population of small nucleic acids that is being normalized and, in some embodiments, being identified. A small nucleic acid can comprise either DNA or RNA and may initially be either single-stranded or double-stranded. Those in the art will appreciate, however, that the disclosed primers anneal with single-stranded polynucleotides, including without limitation one strand of a double-stranded nucleic acid molecule. A small nucleic acid of the current teachings is typically less than 200 nucleotides or base pairs, as appropriate and are often less than 100 nucleotides or base pairs long. In some embodiments, a small nucleic acid is approximately 70 nucleotides or base pairs long. In some embodiments, a small nucleic acid is less than 50 nucleotides of base pairs long, less than 30 nucleotides or base pairs long, less than 25 nucleotides or base pairs long, between 19 and 23 nucleotide or base pairs long, or 21-22 nucleotides or base pairs long, and can but need not include double-stranded molecules with single-stranded overhangs at one or both ends. Some non-limiting examples of small nucleic acid species include small DNA molecules and small RNA molecules, including without limitation certain non-coding DNA (ncDNA, sometimes referred to as non-protein-coding DNA; see, e.g., Bergman and Kreitman, Genome Res. 11:1335-45, 2001) and certain non-coding RNAs (ncRNAs), including without limitation, microRNA precursors (pre-miRNAs), microRNAs (miRNAs) sometimes referred to as small temporal RNAs (stRNAs), small interfering RNAs (siRNAs), tiny noncoding RNAs (tncRNAs), small nucleolar RNAs (snoRNAs), small nuclear RNAs (snRNAs), and spliceosomal RNA (see, e.g., S. Buckingham, Horizon Symposia: Understanding the RNAissance, May 2003, pp. 1-3, Nature Publishing; and Ambros et al., Curr. Biol. 13:807-818, 2003). In some embodiments, the small nucleic acid is present in the nucleus of the cell or in the cytoplasm of the cell, for example but not limited to small nucleic acid species associated with the RISC, miRNP, or ribosomes, including without limitation polyribosomes. Expressly excluded from the term "small nucleic acid" are messenger RNA molecules (mRNA), e.g., (a) typically comprising poly-A tails on their 3'-end, (b) may comprise a "cap structure" that typically includes 7-methylguanosine and can interact with a cap-binding protein (but not always), and (c) serve as templates for protein synthesis, i.e., can be translated by ribosomes to produce peptides. Descriptions of mRNA can be found in, among other places, Lehninger.

II. Techniques

The terms "amplifying" and "amplification" are used in a broad sense and refer to any technique by which at least a part of a adapter-modified molecule or an extension product, is reproduced or copied (including the synthesis of a complementary copy), typically in a template-dependent manner, including without limitation, a broad range of techniques for amplifying nucleic acid sequences, either linearly or exponentially. Some non-limiting examples of amplification techniques include the polymerase chain reaction (PCR) including without limitation RT-PCR and asymmetric PCR, primer extension, strand displacement amplification (SDA), multiple displacement amplification (MDA), nucleic acid strand-based amplification (NASBA), rolling circle amplification (RCA), transcription-mediated amplification (TMA), transcription, and the like, including multiplex versions or combinations thereof. Descriptions of such techniques can be found in, among other places, Sambrook and Russell; Sambrook et al.; Ausubel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); McPherson and Moller, PCR The Basics, Bios Scientific Publishers, Oxford, U.K., 2000 ("McPherson"); Rapley, The Nucleic Acid Protocols Handbook (2000), Humana Press, Totowa, New Jersey ("Rapley"); U.S. Pat. Nos. 6,027,998 and 6,511,810; PCT Publication Nos. WO 97/31256 and WO 01/92579; Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000).

In certain embodiments, amplifying comprises a cycle of the sequential steps of: hybridizing a primer with a complementary or substantially complementary sequence of an adapter-modified molecule or an extension product; synthesizing a strand of nucleotides in a template-dependent manner using a polymerase; and denaturing the newly-formed nucleic acid duplex to separate the strands. The cycle may or may not be repeated, as desired. Amplification can comprise thermocycling or can be performed isothermally. In certain embodiments, newly-formed nucleic acid duplexes are not initially denatured, but are used in their double-stranded form in one or more subsequent steps and either or both strands can, but need not, serve as a surrogate for the corresponding extension product, the corresponding adapter-modified molecule, or ultimately, the corresponding small nucleic acid species. In certain embodiments, single-stranded amplicons are generated, for example but not limited to asymmetric PCR.

Primer extension is an amplifying technique that comprises elongating a primer that is annealed to a template in the 5'=>3' direction using an extending enzyme such as a polymerase to form an extension product. According to certain embodiments, with appropriate buffers, salts, pH, temperature, and nucleotide triphosphates, a polymerase incorporates nucleotides complementary to the template strand starting at the 3'-end of an annealed primer, to generate a complementary strand. In certain embodiments, the polymerase used for primer extension lacks or substantially lacks 5'-exonuclease activity.

A "first extension product" is generated when a first reverse primer, annealed with the corresponding adapter-modified molecule is extended. When the small nucleic acid consists of RNA, the first extension step comprises reverse transcription. A "second extension product" is generated when a first forward primer, annealed with the corresponding first extension product, is extended. A "third extension product" is generated when a second reverse primer, annealed with the corresponding second extension product, is extended. A "fourth extension product" is generated when a third reverse primer, annealed with the corresponding second extension product, is extended. A "fifth extension product" is generated when a second forward primer, annealed with the corresponding fourth extension product, is extended. See, e.g., FIG. 1. The generic term "extension product" refers to a first extension product, a second extension product, a third extension product, a fourth extension product, a fifth extension product, or combinations thereof.

The term "cloning", also referred to as molecular cloning, and derivatives of the root word "clone" are used in a broad sense herein and include any technique known in the art wherein a nucleic acid is inserted into a vector using recombinant methodology and large quantities of the recombinant vector comprising the inserted nucleic acid is produced. Generally such methods comprise constructing a recombinant vector comprising a nucleic acid insert, introducing the recombinant vector into a suitable host cell, selective propagation of host cells containing the vector, and extraction and purification of the cloned nucleic acid. Cloning vectors typically comprise an origin of replication, at least one "cloning cassette" that comprises at least one restriction enzyme cleavage site to facilitate the incorporation of inserts, and at least one selectable marker to facilitate vector and recombinant selection. Some non-limiting examples of vectors include pBR322, ΦX174 RF, pGEM vectors, pSP72 vector, pUC vectors, M13 vectors, TOPO vectors, and λ vectors, many of which are commercially available. In some embodiments, at least part of a second extension product, at least part of a third extension product, at least part of a fourth extension product, at least part of a fifth extension product, or combinations thereof, is cloned into a vector to facilitate identifying the corresponding small nucleic species. In some embodiments, at least one primer species comprises a restriction enzyme cleavage site or its complement to facilitate insertion of at least a part of an extension product in which the restriction enzyme cleavage site becomes incorporated into a vector. Descriptions of cloning and associated techniques can be found in, among other places, Sambrook and Russell, Molecular Cloning, A Laboratory Manual, Cold Spring Harbor Press, 3d ed., 2001 ("Sambrook and Russell"); Ausubel et al.; Twyman, Advanced Molecular Biology, Springer-Verlag New York, 1999, particularly at Chapter 24; Lau et al., Science 294:858-62, 2001; and McPherson, particularly at Chapter 6. Those in the art will appreciate that many well-known techniques can be useful for cloning the normalized extension products of the current teachings and that the vector, cloning technique, or host cells employed are typically not limitations of the current teachings, provided that sufficient nucleic acid is subsequently obtained for identifying the corresponding small nucleic acid.

The terms "denaturing" or "denaturation" as used herein refer to any process in which a double-stranded polynucleotide, including without limitation, a duplex comprising a first extension product annealed with a second extension product, a second extension product annealed with a third extension product, and so forth is converted to two single-stranded polynucleotides. Denaturing a double-stranded polynucleotide includes without limitation, a variety of thermal and chemical techniques for denaturing a duplex, thereby releasing its two individual single-stranded components. Those in the art will appreciate the denaturing technique employed is generally not limiting unless it inhibits a subsequent annealing or identifying step.

The term "degrading" is used in a broad sense herein and refers to any technique in which at least one nucleotide is removed from a nucleic acid molecule or in which at least one internucleotide bond in a nucleic acid molecule is cleaved, including without limitation alkaline hydrolysis and treatment by a nuclease, such as a DNase or an RNase, for example but not limited to exonuclease I, mung bean nuclease, S1 nuclease, exonuclease T, uracil N-glycosylase (UNG, also known as uracil-DNA glycosylase (UDG)), RNase H, RNase I, RNase III, but typically excluding restriction endonuclease cleavage. In some embodiments, a small nucleic acid species is degraded. In some embodiments, an adapter-modified molecule is degraded, for example but not limited to the adapter-modified molecule duplexed with a first extension product. Those in the art will appreciate that the method for degrading nucleic acids is typically not limiting, provided that the desired polynucleotides, typically extension products, are not degraded or at least not substantially degraded, while the small nucleic acids and/or adapter-modified molecules are degraded. In some embodiments, a primer comprises a uracil or a deoxyuracil. In some embodiments, unincorporated primers and/or dNTPs are removed by enzymatic degradation, including without limitation treatment with exonuclease I and shrimp alkaline phosphatase digestion, for example but not limited to the ExoSAP-IT® reagent (USB Corporation) or UNG. In some embodiments, unincorporated primers and/or dNTPs are removed by gel or column purification, sedimentation, filtration, beads, magnetic separation, or hybridization-based pull out, for example but not limited to a Wizard® MagneSil™ PCR Clean-Up System (Promega), a MinElute PCR Purification Kit, a QIAquick Gel Extraction Kit, a QIAquick Nucleotide Removal Kit, a QIAquick 96 PCR Purification Kit or BioRobot Kit (all from Qiagen, Valencia, Calif.), or an ABI PRISM® Duplex™ 384 Well F/R Sequence Capture Kit (Applied Biosystems P/N 4308082).

Ligation according to the present teachings comprises any enzymatic or non-enzymatic means wherein an inter-nucleotide linkage is formed between appropriate ends of nucleic acid sequences, including without limitation, the 5'-end of a 3' adapter and the 3'-end of a small nucleic acid provided that they are suitable for ligation together, and including blunt end ligation. The internucleotide linkage can include, but is not limited to, phosphodiester bond formation. Such bond formation can include, without limitation, those created enzymatically by a DNA ligase or an RNA ligase capable of catalyzing blunt-end ligation. Other internucleotide linkages include, without limitation, covalent bond formation between appropriate reactive groups such as between an α-haloacyl group and a phosphothioate group to form a thiophosphorylacetylamino group, a phosphorothioate a tosylate or iodide group to form a 5'-phosphorothioester, and pyrophosphate linkages.

Chemical ligation can, under appropriate conditions, occur spontaneously such as by autoligation. Alternatively, "activating" or reducing agents can be used. Examples of activating and reducing agents include, without limitation, carbodiimide, cyanogen bromide (BrCN), imidazole, 1-methylimidazole/carbodiimide/cystamine, N-cyanoimidazole, and dithiothreitol (DTT).

According to the present teachings, the term "normalizing" refers to a method in which (a) the relative concentration of at least one small nucleic acid species in a group comprising a multiplicity of different nucleic acid species (for example but not limited to a population of different small nucleic acid species in varying concentrations, a multiplicity of different adapter-modified molecules, or a multiplicity of different extension products or amplicons) is decreased relative to at least one other nucleic acid species in the group, (b) the relative concentration of at least one small nucleic acid in the group is increased relative to at least one different nucleic acid species in the group, or (c) both. The term "normalized" when used in reference to a population of different nucleic acid species refers to a multiplicity of different nucleic acid species that have been subjected to at least one round of normalizing and therefore comprises at least one nucleic acid species whose relative concentration has been increased or decreased compared with at least one other nucleic acid species in the original group of different small nucleic acid species. Thus, the relative concentrations of the different extension products are often at least similar, if not the same after normalization. It is to be understood that even though surrogates of the small nucleic acid species present in the original population are being normalized (e.g., adapter-modified molecules and/or extension products), the resulting normalized population typically reflects the composition of the original population qualitatively, but not quantitatively. A "normalized nucleic acid" is a nucleic acid sequence, typically an extension product, that is present in a normalized population.

According to the present teachings, a normalized population can be obtained using a multiplicity of different primer species, wherein at least some of the different primer species comprise a degenerate sequence at the 3'-end of the primer. Thus, normalizing is based on the nucleotide sequences that are present at the 3'-end and/or the 5'-end of small nucleic acids (typically the last 6, 5, 4, 3, 2, or 1 nucleotides on each end) or their surrogates, including in some embodiments, the complement of such "end" sequences. In some embodiments, normalized populations are generated by normalizing the 3'-ends of the small nucleic acids or their surrogates; in some embodiments, normalized populations are generated by normalizing the 5'-ends of the small nucleic acids or their surrogates; in some embodiments, normalized populations are generated by normalizing the 3'-ends and the 5'-ends of the small nucleic acids or their surrogates.

The term "sequencing" is used in a broad sense herein and refers to any technique known in the art that allows the order of at least some consecutive nucleotides in at least part of a polynucleotide to be identified, including without limitation at least part of an extension product or a vector insert. Some non-limiting examples of sequencing techniques include Sanger's dideoxy terminator method and the chemical cleavage method of Maxam and Gilbert, including variations of those methods; sequencing by hybridization; and restriction mapping. Some sequencing methods comprise electrophoreses, including without limitation capillary electrophoresis and gel electrophoresis; sequencing by hybridization including without limitation microarray hybridization; mass spectrometry; and single molecule detection. In some embodiments, sequencing comprises direct sequencing, duplex sequencing, cycle sequencing, single base extension sequencing (SBE), solid-phase sequencing, 3' exonuclease sequencing; cleavage fragment length polymorphism sequencing; microtransponder-based sequencing; or combinations thereof. Those in the art will appreciate that the sequencing method employed is not typically a limitation of the present methods. Rather any sequencing technique that provides the order of at least some consecutive nucleotides of at least part of the corresponding extension product or at least part of a vector insert derived from an extension product can typically be used with the current methods. Descriptions of sequencing techniques can be found in, among other places, McPherson, particularly in Chapter 5; Sambrook and Russell; Ausubel et al.; Siuzdak, The Expanding Role of Mass Spectrometry in Biotechnology, MCC Press, 2003, particularly in Chapter 7; Datar and Kim, Concepts in Molecular Biology, Eaton Publishing, 2003; and Rapley. In some embodiments, unincorporated primers and/or dNTPs are removed prior to a sequencing step by enzymatic degradation, including without limitation UNG or exonuclease I and shrimp alkaline phosphatase digestion, for example but not limited to the ExoSAP-IT® reagent (USB Corporation). In some embodiments, unincorporated primers and/or dNTPs are removed by gel or column purification, sedimentation, filtration, beads, magnetic separation, or hybridization-based pull out (see, e.g., ABI PRISM® Duplex™ 384 Well F/R Sequence Capture Kit, Applied Biosystems P/N 4308082).

III. Exemplary Embodiments

Certain embodiments of the present teachings comprise combining a multiplicity of adapters with a multiplicity of different small nucleic acid species of varying abundance and ligating at least one adapter to a small nucleic acid to generate a multiplicity of different adapter-modified molecules. In some embodiments, adapter-modified molecules are amplified to generate first extension products before normalization. The multiplicity of different adapter-modified molecules or corresponding extension products are subjected to at least one round of normalization using at least one primer species comprising a degenerate sequence, thereby generating a normalized population. Some methods comprise at least two rounds of normalization, typically one round of normalization directed to the 5'-end of a nucleic acid species or its surrogate and one round of normalization directed to the 3'-end of a corresponding nucleic acid species or its surrogate. Those in the art will appreciate that an adapter-modified molecule, a first extension product, a second extension product, a third extension product, a fourth extension product, a fifth extension product, or combinations thereof, and including portions of any of these extension products, can serve as a surrogate of the corresponding small nucleic acid species.

The adapters of the present teachings comprise a primer-binding site and in some embodiments, a blocking moiety. The primer-binding site comprises a sequence that is the same as or is complementary to at least a portion of a forward primer or a reverse primer. In some embodiments, the primer-binding portion comprises a universal priming sequence, allowing amplification of at least some extension products with a universal primer or a universal primer pair. According to the disclosed methods, a ligation composition comprising a multiplicity of adapters, a population of different nucleic acid species, and a ligation agent is formed. In some embodiments, the ligation composition further comprises ATP to support ATP-mediated ligation. In some embodiments, the population of small nucleic acid species is treated with a phosphatase, such as calf intestinal phosphatase (CIP). In some embodiments, the multiplicity of adapters comprises a multiplicity of 5' adapters or a multiplicity of 3' adapters, but not both. In other embodiments, the multiplicity of adapters comprises a multiplicity of adapter pairs, comprising a multiplicity of 5' adapters and a multiplicity of 3' adapters. Provided that at least some of the adapters are suitable for ligation with the small nucleic acids and under appropriate reaction conditions, one or two adapters are ligated with a small nucleic acid to form an adapter-modified molecule. In some embodiments, at least some of the adapters comprise a blocking moiety on one end of the adapter, for example but not limited to a dideoxy moiety or a 4-hydroxymethylbenzyl moiety on the 3'-end of an adapter, which render those adapter ends unsuitable for enzymatic ligation. In some embodiments, an adapter comprises a phosphorylated 5'-end. In some embodiments, an adapter comprises a 3'-end comprising a hydroxyl group, a 5'-end comprising a hydroxyl group, or both. In some embodiments, adapters comprise at least one restriction enzyme cleavage site. In some embodiments, an adapter is pre-activated with an adenylyl group. In some embodiments, an adapter comprises deoxyribonucleotides, but not ribonucleotides. In some embodiments, an adapter comprises ribonucleotides, but not deoxyribonucleotides. In some embodiments, an adapter comprises deoxyribonucleotides and ribonucleotides. In some embodiments, an adapter comprises at least one ribonucleotide, at least two ribonucleotides, or at least three ribonucleotides on the end to be ligated with a small nucleic acid, e.g., the 3'-end of a 5' adapter, the 5'-end of the 3' adapter, or both.

Some embodiments of the disclosed methods comprise a multiplicity of different first reverse primer species, wherein at least some of the different first reverse primer species comprise a degenerate sequence and wherein the degenerate sequence of at least one first reverse primer species is different from the degenerate sequence of at least one other first reverse primer species. Some embodiments of the present teachings comprise a multiplicity of different second reverse primer species, wherein at least some of the different second reverse primer species comprise a degenerate sequence and wherein the degenerate sequence of at least one second reverse primer species is different from the degenerate sequence of at least one other second reverse primer species. Some embodiments comprise a multiplicity of different third reverse primer species, wherein at least some of the different third reverse primer species comprise a degenerate sequence and wherein the degenerate sequence of at least one third reverse primer species is different from the degenerate sequence of at least one other third reverse primer species; and so forth. Some embodiments of the present teachings comprise a multiplicity of different first forward primer species, wherein at least some of the different first forward primer species comprise a degenerate sequence and wherein the degenerate sequence of at least one first forward primer species is different from the degenerate sequence of at least one other first forward primer species. Some embodiments of the present teachings comprise a multiplicity of different second forward primer species, wherein at least some of the different second forward primer species comprise a degenerate sequence and wherein the degenerate sequence of at least one second forward primer species is different from the degenerate sequence of at least one other second forward primer species; and so forth. In some embodiments, a primer species comprising a degenerate sequence further comprises a "stem-loop" structure. In some embodiments, a degenerate sequence (a) comprises, consists essentially of, or consists of (b) one, two, three, four, five, or six nucleotides.

In some embodiments, only a subset of the possible degenerate sequences are included in an amplification composition, typically to avoid primer dimer formation between two different primer species that comprise complementary or substantially complementary degenerate sequences. For illustration purposes but not as a limitation, assume a multiplicity of different third forward primer species each comprising a different degenerate sequence consisting of three nucleotides, in which case, a library of 64 different degenerate sequences are possible ($4^3=64$). If 64 different third forward primer species, each comprising one of the 64 different degenerate sequences were combined in an amplification composition, at least some primer dimers could form. However, by employing a subset of those 64 different degenerate sequences in the amplification composition, wherein complementary or substantially complementary degenerate sequences are not included, the potential for primer dimer formation is decreased. Thus, for example, one amplification composition could comprise a third forward primer species comprising a degenerate sequence consisting of "GTA" but not the third forward primer species comprising the degenerate sequences consisting of "TAC". The entire library of different degenerate sequences can be employed in a multiplicity of different amplification compositions, each comprising a different subset of possible degenerate sequences. For example but without limitation, a library of 256 different possible degenerate sequences ($4^4=256$) could be employed in two different amplification compositions, each comprising a mutually exclusive subset of 128 different degenerate sequences; in four different amplification compositions, each comprising a mutually exclusive subset of 64 different degenerate sequences; and so forth. Various permutations thereof are also within the contemplation of the current teachings, for example but not limited to, one amplification composition comprising 128 different degenerate sequences, one amplification composition comprising 99 different degenerate sequences, and one amplification composition comprising 29 different degenerate sequences. Those in the art will appreciate that the number of different subsets and the degree of subset exclusivity required to effectively address primer dimer formation and secondary amplicon artifacts can be determined using routine methodology, without resort to undue experimentation. In some embodiments, portions of the ligation composition comprising the multiplicity of different adapter-modified molecules are normalized in parallel amplification compositions, each comprising a different subset of primers comprising degenerate sequences. In some embodiments, not all possible degenerate sequences are employed or are employed in separate reactions, e.g., not performed in parallel.

Certain disclosed primers comprise a binding portion that is designed to anneal with a complementary or substantially complementary binding site in a corresponding surrogate, for example but not limited to an adapter-modified molecule or an extension product. These binding portions, typically comprising nucleotides at the 5'-end of the primer, internal nucleotides, or both, are of sufficient length to permit specific annealing to complementary or substantially complementary sequences in corresponding surrogates. In some embodiments, a primer comprises a binding portion and a 5' tail sequence for incorporating additional sequences into the corresponding extension products, for example but not limited to a promoter sequence. The criteria for designing sequence-specific nucleic acid primers are well known to persons of ordinary skill in the art. Detailed descriptions of primer design can be found in, among other places, Diffenbach and Dveksler, PCR Primer, A Laboratory Manual, Cold Spring Harbor Press (1995); Rapley; Schena; and Kwok et al., Nucl. Acid Res. 18:999-1005 (1990). Primer design software is also commercially available from a variety of vendors. In some embodiments, at least part of the binding portion of a multiplicity of different primers comprise a universal priming sequence, which allows the potential use of universal primers in at least one subsequent amplification step. Universal primers/priming sequences (also known as generic primers), including without limitation M13 universal primers and T7 universal primers, and their use are well known in the art (see, e.g., McPherson, particularly section 4.2 of Chapter 5). In some embodiments, a universal primer or a pair of universal primers can be employed as sequencing primers for a subsequent sequencing step; and either or both strands of a double-stranded molecule can be sequenced, for example, a second extension product:third extension product duplex or a nucleic acid insert in certain vectors (see, e.g., McPherson, particularly section 4 of Chapter 5). In some embodiments, a sequencing primer comprises the nucleotide sequence present in an adapter-modified molecule that corresponds to a junction between the ligated adapter and the small nucleic acid, or the complement of that sequence. Typically such sequencing primers comprise at least some nucleotides that correspond with the appropriate end of the small nucleic acid species and at least as many nucleotides that correspond with the adapter sequence (or the complement of that sequence) to permit specific annealing. In some embodiments, a sequencing primer comprises six, five, four, three, two, or one nucleotides that correspond with the end of the small nucleic acid sequence, i.e., either the same as or complementary to the end of the small nucleic acid species.

It is to be understood that when a small nucleic acid species comprises ribonucleotides, for example but not limited to a miRNA species, a primer comprising a sequence that is the same as or complementary to that species of small nucleic acid typically comprises deoxyribonucleotide counterparts of the corresponding small RNA species. In some embodiments, a sequencing primer comprises a sequence that is the same as or is complementary to a region of an extension product that corresponds to an adapter-small nucleic acid molecule junction of an adapter-modified molecule and such primers can include deoxyribonucleotide counterparts of ribonucleotides present in either the small nucleic acid or in the adapter, for example but not limited to a hybrid adapter comprising both ribonucleotides and deoxyribonucleotides, or both. For the purposes of the present teachings, however, such primers are considered to comprise a sequence that is the same as or complementary to at least a part of the small nucleic acid species or the adapter-small nucleic acid junction, respectively.

Certain methods for normalizing a population of different small nucleic acid species of varying abundance comprise forming a ligation composition comprising a multiplicity of different small nucleic acid sequences, a multiplicity of adapters, and a ligation agent. In some embodiments, the multiplicity of adapters comprises a multiplicity of 5' adapters or a multiplicity of 3' adapters, but typically not both. In some embodiments, the multiplicity of adapters comprises a multiplicity of adapter pairs, comprising a multiplicity of 5' adapters and a multiplicity of 3' adapters. In some embodiments, adapters comprise a chimeric sequence including both deoxyribonucleotides and ribonucleotides. A multiplicity of different adapter-modified molecules are generated in the ligation composition when at least some of the multiplicity of adapters are ligated to at least some of the multiplicity of small nucleic acids. A first amplification reaction composition is formed comprising at least some of the different adapter-modified molecules, a first extending enzyme, and a multiplicity of reverse primers. In some embodiments, a reverse primer can form a hairpin or stem-loop structure. At least some of the first reverse primers anneal with corresponding regions of at least some of the multiplicity of different adapter-modified molecules and are extended by the first extending enzyme to generate duplex structures comprising the adapter-modified molecule annealed to the corresponding first extension product.

According to certain disclosed methods, a ligation composition is formed comprising a multiplicity of adapter pairs, a population of different small nucleic acid species, and a ligation agent. The concentration of at least one of the species of small nucleic acid molecules in the population is substantially greater than the concentration of at least one other small nucleic acid species in the population. An adapter pair of the present teachings comprises a 3' adapter comprising a first primer-binding site and a 5' adapter comprising a second primer-binding site. Double adapter-modified molecules are generated in the ligation composition when a 5' adapter is ligated to the 5'-end of a small nucleic acid and a 3' adapter is ligated to the 3'-end of the same small nucleic acid. In some embodiments, forming a double adapter-modified molecule comprises two steps, first ligating a 3' adapter with a small nucleic acid to generate a single adapter-modified molecule, wherein the 3' adapter comprises a blocked 3'-end and is pre-activated with an adenylyl group on the 5'-end; then ligating a 5' adapter to the 5'-end of the single adapter-modified molecule to generate a double adapter-modified molecule.

A first amplification composition is formed comprising at least some of these double adapter-modified molecules, a first extending enzyme, including without limitation an RNA-dependent DNA polymerase such as a reverse transcriptase, and a multiplicity of first reverse primers. The first reverse primers comprise a sequence that is complementary with the first primer-binding site of the double adapter-modified molecules. At least some of the first reverse primers are annealed with at least some of the double adapter-modified molecules. At least some of the annealed first reverse primers are extended by the first extending enzyme to generate a multiplicity of different first extension products, each duplexed with the corresponding double adapter-modified molecule. In some embodiments, the duplexes comprising the different first extension products hybridized with the adapter-modified molecules are denatured, including without limitation, thermal or chemical denaturation. In some embodiments, a small nucleic acid, a primer, an adapter-modified molecule, or combinations thereof is degraded, for example but not limited to an adapter-modified molecule duplexed with a first extension product or an unincorporated primer. In some embodiments, degrading comprises subjecting the first amplification composition comprising first extension products to alkaline hydrolysis or nuclease digestion.

In some embodiments, a second amplification reaction composition is formed comprising: at least some of the first amplification composition comprising the different first extension products, a second extending enzyme, and a formulated relative concentration of primers comprising a multiplicity of different first forward primer species and a second reverse primer species. In some embodiments, the first amplification composition comprising extension products is diluted. The first amplification composition can be diluted in buffer, for example, and a portion of the diluted first amplification composition added to the second amplification composition being formed. In some embodiments, a portion of undiluted first amplification composition is diluted when it is added to the second amplification composition being formed. In some embodiments, all of the first reaction composition comprising first extension products is added to the second amplification composition, wherein it is diluted. Each of the different first forward primer species of the second amplification composition comprises (a) a sequence that is complementary to the second primer-binding site of the first extension products and (b) a degenerate sequence that is located at the 3'-end of the first forward primer and that comprises at least two nucleotides. The degenerate sequence of one first forward primer species is typically different from the degenerate sequence of the other first forward primer species. The second reverse primer of the second amplification composition comprises a sequence that is the same as or substantially the same as the first primer-binding site of the first extension product.

The second amplification composition is subjected to denaturing conditions to separate the adapter-modified molecules from the multiplicity of different first extension products. At least some of the first forward primer species anneal with at least some of the different first extension products in the second reaction composition. At least some of the annealed first forward primers are extended by the second extending enzyme and a multiplicity of different second extension products, duplexed with their first extension product templates, are generated. In some embodiments, the first extending enzyme and the second extending enzyme are the same, while in other embodiments, the first extending enzyme and the second extending enzyme are different, for example but not limited to a reverse transcriptase and a DNA-dependent DNA polymerase, such as Taq polymerase. The second amplification composition is subjected to denaturing conditions to release at least some of the different second extension products and then at least some of the second reverse primers anneal with at least some of the second extension products. At least some of the annealed second reverse primers are extended by the second extending enzyme and a multiplicity of different third extension products, duplexed with their second extension product templates are generated. In some embodiments, the cycle of annealing and extending additional first forward primers to generate more second extension products and annealing and extending additional second reverse primers to generate more third extension products, is repeated, typically multiple times and typically comprising thermocycling.

In some embodiments, the sequence of at least part of a second extension product, the sequence of at least part of a third extension product, or combinations thereof, is determined and the corresponding small nucleic acid species is identified. In some embodiments, the nucleotide sequence of at least part of a second extension product and/or at least part of a third extension product is determined by sequencing at least part of the corresponding extension product. In some embodiments, the determining comprises cloning.

In some embodiments, a third amplification composition is formed comprising at least part of the second amplification composition comprising second and third extension products, a third extending enzyme, and a formulated relative concentration of a second forward primer and a multiplicity of different third reverse primers. In some embodiments, the second amplification composition comprising extension products is diluted. The second amplification composition can be diluted in buffer, for example, and a portion of the diluted second amplification composition added to the third amplification composition being formed. In some embodiments, a portion of undiluted second amplification composition is diluted when it is added to the third amplification composition being formed. In some embodiments, all of the second reaction composition comprising second and third extension products is added to the third amplification composition, wherein it is diluted. The second forward primer comprises a sequence that is the same as or substantially the same as the second primer-binding site of the second extension products. The third reverse primers comprise (a) a sequence that is the same or substantially the same as the first primer binding site of the third extension products and (b) a degenerate sequence, located at the 3'-end of the third reverse primer, comprising at least two nucleotides. The degenerate sequence of one third reverse primer species is different from the degenerate sequence of other third reverse primer species.

The third amplification composition is subjected to denaturing conditions to release the duplexed second and third extension products. At least some of the different third primers anneal with at least some of the second extension products (i.e., one third primer anneals with one second extension product) in the third amplification composition. At least some of the annealed third reverse primers are extended by the third extending enzyme to generate a multiplicity of different fourth extension products, duplexed with the corresponding second extension product template. These duplexes are denatured, releasing the second and fourth extension products which can then serve as templates in additional amplification reactions. At least some of the different fourth extension products anneal with at least some of the second forward primers. At least some of the annealed second forward primers are extended by the third extending enzyme, generating a multiplicity of different fifth extension products, duplexed with their corresponding fourth extension products. In some embodiments, the first extending enzyme and the second extending enzyme are the same or different. In some embodiments, the second extending enzyme and the third extending enzyme are the same or different.

In some embodiments, the sequence of at least part of a second extension product, at least part of a third extension product, at least part of a fourth extension product, at least part of a fifth extension product, or combinations thereof, are determined and the corresponding small nucleic acid is identified. In some embodiments, identifying a small nucleic acid species comprises cloning at least part of an extension product corresponding to the small nucleic acid, for example but not limited to a restriction fragment of that extension product. In some embodiments, an extension product or at least part of an extension product is inserted into a recombinant vector and the vector is introduced into an appropriate host cell and amplified in vivo. The amplified vectors are isolated from the host cells and the nucleotide sequence of the inserts, comprising at least part of the sequence of an extension product or its complement, are determined using sequencing methods known in the art.

In some embodiments, a "size fractionation" or other pre-selection procedure is performed on the sample, for example but not limited to subjecting "total RNA" to gel electrophoresis, excising the band or collecting the eluate from the gel that corresponds to nucleic acids of a desired range of weight or length; using a sample preparation kit, such as the mirVana™ miRNA Isolation Kit according to the enrichment procedure for small RNAs (Ambion, Austin, Tex.) or the PureLink™ miRNA Isolation Kit (Invitrogen, Carlsbad, Calif.). In some embodiments, a population of different small nucleic acid species of varying concentration is obtained by copurifying the small nucleic acids with other cellular components or organelles, including without limitation polyribosomes, RNA induced silencing complex (RISC) or other intracellular RNPs such as the miRNP complex, or nuclei (see, e.g., Elbashir et al., Genes and Development, 15:188-200, 2001; and Kim et al., Proc. Natl. Acad. Sci. 101:360-65, 2004). In other embodiments, crude lysates are obtained from cells according to known methods, for example by heating at 95 C.° for 5 minutes, sonication, or in a lysis reagent, such as a Tris lysate buffer (e.g., 10 mM Tris-HCl, pH 8.0, 0.02% sodium azide, and 0.03% Tween-20) or a GuHCl lysis buffer (e.g., 2.5M GuHCl, 150 mM MES pH 6.0, 200 mM NaCl, 0.75% Tween-20), among others (see, e.g., U.S. Provisional Patent Application Ser. No. 60/643,180, which is expressly incorporated by reference). All pre-treated biological materials, including without limitation, enriched fractions, lysates, and so forth can be the source of the population of different small nucleic acid species. Additionally, the population of different small nucleic acid species can be derived from a human or from a non-human species, including without limitation, vertebrate species, for example but not limited to mouse, rat, hamster, dog, cat, pig, or various primate species; invertebrate species, for example but not limited to, *Caenorhabditis elegans* and *Drosophila melanogaster*; plant species, for example but not limited to, *Arabidopsis thaliana*; or viruses.

Figure 1:
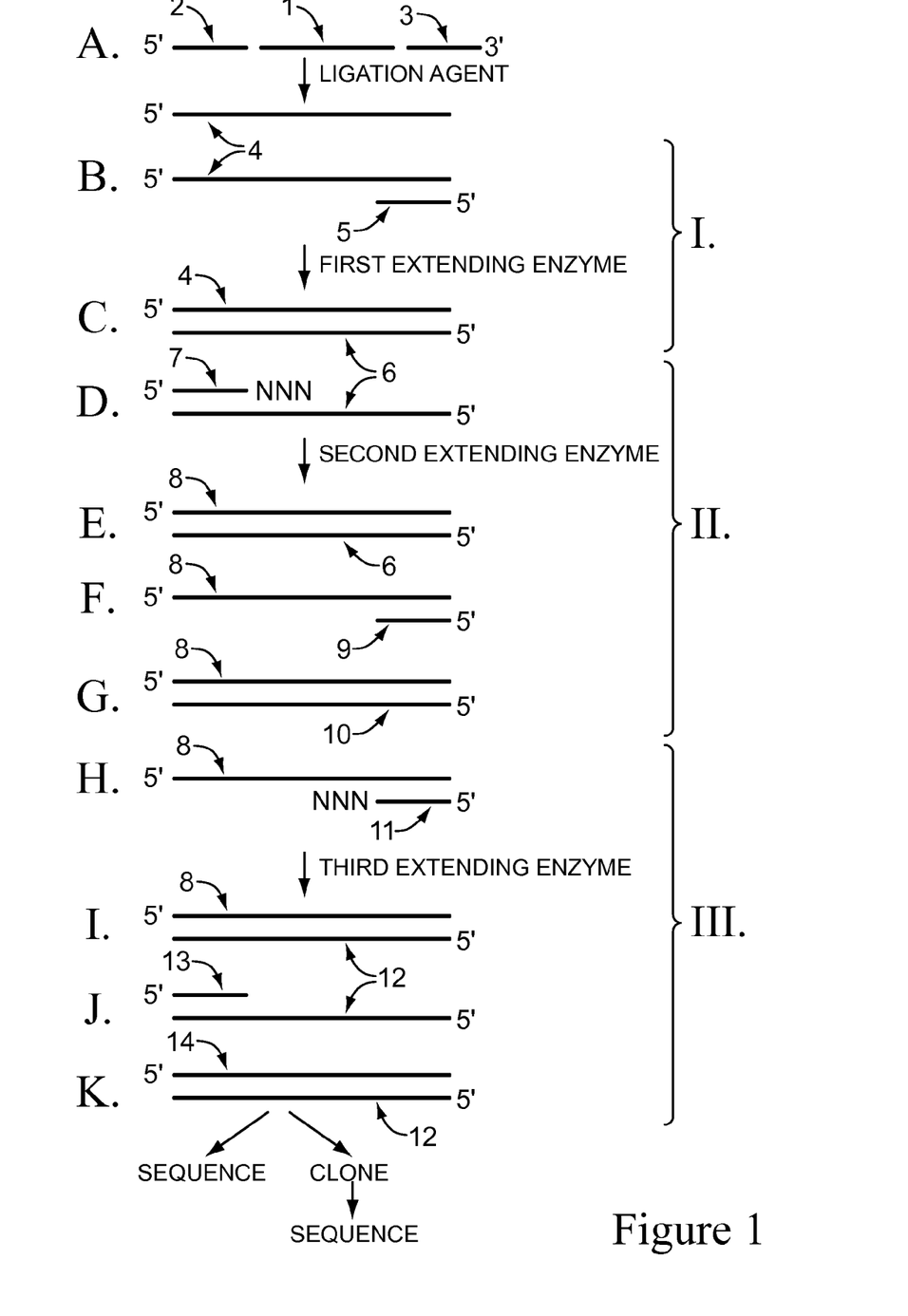
FIG. 1: depicts an illustrative embodiment of certain disclosed methods comprising double adapter-modified molecules.

FIG. 1 schematically depicts one illustrative embodiment of the present teachings. A multiplicity of different small nucleic acids (1) are combined with a multiplicity of 5' adapters (2), a multiplicity of 3' adapters (3), and a ligation agent. A multiplicity of double adapter-modified molecules (4) is generated by ligating the two adapters to the respective ends of the same small nucleic acid sequence, as shown in panel A. A first amplification composition (I) is formed comprising at least some of the double adapter-modified molecules (4), a multiplicity of first reverse primers (5), and a first extending enzyme, for purposes of this illustrative embodiment, AMV reverse transcriptase. At least some of the multiplicity of first reverse primers (5) anneal with at least some of the double adapter-modified molecules (4), as shown in panel B. The annealed first reverse primers (5) are extended by the first extending enzyme to generate a multiplicity of duplexes, each comprising a newly synthesized first extension product (6) annealed with the corresponding adapter-modified molecule (4), as shown in panel C. A second amplification composition (II) is formed comprising at least some of the multiplicity of different first extension products (6), a multiplicity of different first forward primer species (7), each comprising a degenerate sequence (depicted as "NNN"), a multiplicity of second reverse primers (9), and a second extending enzyme, for purposes of this illustrative embodiment, AmpliTaq Gold® polymerase. At least some of the different first forward primer species (7) anneal the corresponding first extension products (6), as shown in panel D. Those in the art will appreciate that the specificity of first forward primer annealing is determined, at least in part, by the actual sequence of the first degenerate sequence. At least some of the annealed first forward primers (7) are extended by the second extending enzyme to generate a multiplicity of different duplexes, each comprising a newly synthesized second extension product (8) annealed with the corresponding first extension product (6), as shown in panel E. The second amplification composition comprising the multiplicity of different second extension products is subjected to denaturing conditions, releasing at least some of the multiplicity of different second amplification species. At least some of the second reverse primers (9) anneal with at least some of the different second extension products (8), as shown in panel F, and the at least some of the annealed primers are extended to generate a multiplicity of duplexes, each comprising a newly synthesized third extension product (10) hybridized with the corresponding second extension product (8), as shown in panel G.

In some embodiments, primer pairs are employed at a formulated relative concentration, for example but not limited to, the concentration of each of the different first forward primer species in a second amplification composition may initially be equimolar or at least similar and the starting concentration of the second reverse primer species is greater than the total concentration of the different first primer species. For illustration purposes but not as a limitation, consider a multiplicity of different first forward primer species comprising a degenerate sequence consisting of three nucleotides including 64 ($4^3$) different first forward primer species. If all of the 64 different first forward primer species are employed in an amplification composition with a single second reverse primer species, an illustrative formulated relative concentration might comprise (a) the 64 different first forward primer species at a concentration of 1 nm each (i.e., a total first forward primer concentration of 64 nM) and (b) a single second reverse primer species at a concentration of at least 100 nM. Assuming that the amplification composition is cycled until at least one first forward primer species is depleted, the pool of different second extension products should theoretically not contain more than 1 nM of any individual second extension product species and may contain less if more than one small nucleic acid species comprise the same three nucleotide sequence at their 5'-end. Therefore, a first stage of normalization has occurred because the group of different small nucleic acids comprised at least one species that was present at an initial concentration that was substantially greater than the initial concentration of at least one other small nucleic acid species, but none of the second extension product species should have a concentration of greater than 1 nM and most of the second extension product species should have a concentration of about, or relatively close to, 1 nM, for example but not limited to, 0.5 nM, 0.333 nM, 0.25 nM, 0.2 nM, and 0.1667 nM.

Returning to FIG. 1, a third amplification composition (III) is formed, comprising at least some of the different extension products, a multiplicity of different third reverse primer species (11), each comprising a degenerate sequence (shown as "NNN"), a multiplicity of second forward primers (13), and a third extending enzyme, for this illustrative embodiment, AmpliTaq Gold® polymerase. The third amplification composition is subjected to denaturing conditions to denature at least some duplexes. At least some of the third reverse primers (11) anneal with the corresponding second extension product (8), as shown in panel H. Those in the art will appreciate that the specificity of third reverse primer annealing is determined, at least in part, by the actual sequence of the corresponding degenerate sequence. At least some of the annealed third reverse primers (11) are extended by the third extending enzyme to generate a multiplicity of different duplexes, each comprising a newly synthesized fourth extension product (12) annealed with the corresponding second extension product (8), as shown in panel I. The third amplification composition is subjected to denaturing conditions to denature at least some of the duplexes. At least some of the released fourth extension products (12) anneal with at least some of the second forward primers (13), as shown in panel J. At least some of the annealed second forward primers (13) are extended by the third extending enzyme to generate a multiplicity of different duplexes, each comprising a newly synthesized fifth extension product (14) hybridized with the corresponding fourth extension product (12), as shown in panel K. At least a part of a second extension product, at least part of a third extension product, at least part of a fourth extension product, at least part of a fifth extension product, or combinations thereof can be sequenced to identify the corresponding small nucleic acid sequence in the population of different small nucleic acid species (shown in FIG. 1 as "SEQUENCE"). In some embodiments, at least part of a second extension product, at least part of a third extension product, at least part of a fourth extension product, at least part of a fifth extension product, or combinations thereof, is inserted into a cloning vector; the vector comprising the insert is amplified in vivo; the cloned inserts are sequenced, and the identity of the small nucleic acid sequence corresponding to the insert is established (shown in FIG. 1 as "CLONE→SEQUENCE").

Assuming that: 1) the initial concentration of a second extension product species is different from the initial concentration of another second extension product species, for example but not limited to the concentration of at least one second extension product species might be about 1 nM, while the initial concentration of at least one other second extension product species might be about 0.5 nM, about 0.333 nM, about 0.25 nM, and so forth; 2) the initial concentration of each of the different third reverse primer species in the third amplification composition are equimolar (or at least similar) and 3) the starting concentration of the second forward primers is in excess compared to each of the different third reverse primer species and in excess of the total third reverse primer concentration; a second normalization can occur in the third amplification composition.

For illustration purposes but not as a limitation, assume a group of three different small nucleic acid species is being normalized and identified, wherein species 1, with the sequence ugagguaggauguuguauaguu (SEQ ID NO:1), is present in the population at an initial concentration of 500,000 copies; species 2, with the sequence uaucacagccucgu-uugaugugc (SEQ ID NO:3), is present in the population at an initial concentration of 8,000 copies; and species 3, with the sequence uagcagccacgaauaauuggcg (SEQ ID NO:3), is present in the population at an initial concentration of 8,000 copies. The primers are used in a formulated relative concentration in which (a) the multiplicity of different first forward primer species includes 16 different first forward primer species each with a different degenerate sequence consisting of two nucleotides and each at an initial concentration of about 3 nM (total first forward primer concentration of about 48 nM); and (b) the second reverse primer species is initially present at an initial concentration of about 80 nM. After the second amplification composition has been cycled until at least one first forward primer species has been depleted, the concentration of the second extension product corresponding to small nucleic acid species 1 should theoretically be about 3 nM. The concentrations of the second extension product corresponding to small nucleic acid species 2 and to small nucleic acid species 3 should theoretically be about 1.5 nM each because they both have the same two ribonucleotides at the 5'-end (ua) and both small nucleic acid species had the same initial copy number. Thus, normalization has occurred in the second amplification composition since the concentration ratio of species 1 relative to species 2 and 3 was initially 500,000:8000:8000 (250:4:4), but the concentration ratio of the second extension products corresponding to species 1 relative to the second extension products corresponding to species 2 and species 3 is 2:1:1, respectively. Continuing this illustration, a second stage of normalization can be performed in a third reaction composition comprising primers in a formulated relative concentration, e.g., 16 different third reverse primer species each comprising a second degenerate sequence consisting of two nucleotides, at initial concentrations of 2 nM each and a second forward primer species at an initial concentration of 60 nM. After the third amplification composition has been cycled until at least one third reverse primer species is depleted, the concentration of each of the fourth extension products (and fifth extension products) should theoretically be 2 nM, since the three small nucleic acid species in the exemplary population each have different terminal and penultimate nucleotides at their respective 3'-ends. Those in the art will appreciate that certain embodiments of the present teachings, provide means for sequencing and identifying, or for cloning, sequencing and identifying, small nucleic acid species that are initially present in a population at extremely low copy number.

Some embodiments of the present teachings employ a multiplicity of different first reverse primer species, wherein at least some of the first reverse primer species comprise a degenerate sequence and a "stem-loop" or "hairpin" structure that typically serves as at least part of a primer-binding site. In one exemplary embodiment, shown in FIG. 2, a ligation composition is formed comprising a population of different small nucleic acid species of varying concentration, a multiplicity of 5' adapters, and a ligation agent. As shown in panel A, a small nucleic acid (21) and a 5' adapter (22) are ligated together by the ligation agent to from a single adapter-modified molecule (23). A first amplification composition is formed comprising a multiplicity of different single adapter-modified molecules, a multiplicity of different first reverse primer species, and a first extending enzyme. As shown in panel B, a first reverse primer (24) comprising a degenerate sequence (shown as "NNN") and a stem-loop structure anneals with the corresponding single adapter-modified molecule (23) and the annealed first reverse primer is extended by the first extending enzyme to generate a duplex comprising a newly synthesized first extension product (25) hybridized with the single adapter-modified molecule (23), as shown in panel C. Following this first round of normalization, the multiplicity of different first extension product species reflects a normalized population in that the relative concentration of at least one nucleic acid species (as measured by the corresponding first extension product) has been decreased, the relative concentration of at least one other nucleic acid species (as measured by its corresponding extension product) has been increased, or both. The duplexes are diluted in buffer and an portion added to a second amplification composition that comprises a second extending enzyme and a formulated relative concentration of primers comprising a first forward primer species (26) and a multiplicity of different second reverse primer species (28). Each of the second reverse primer species comprises a second degenerate sequence (also shown as "NNN") that is different from the second degenerate sequence of the other second reverse primer species. The concentration of the first forward primer species is greater than the total concentration of the multiplicity of different second reverse primer species and the concentration of each of the different second reverse primer species is approximately equimolar.

Figure 2:
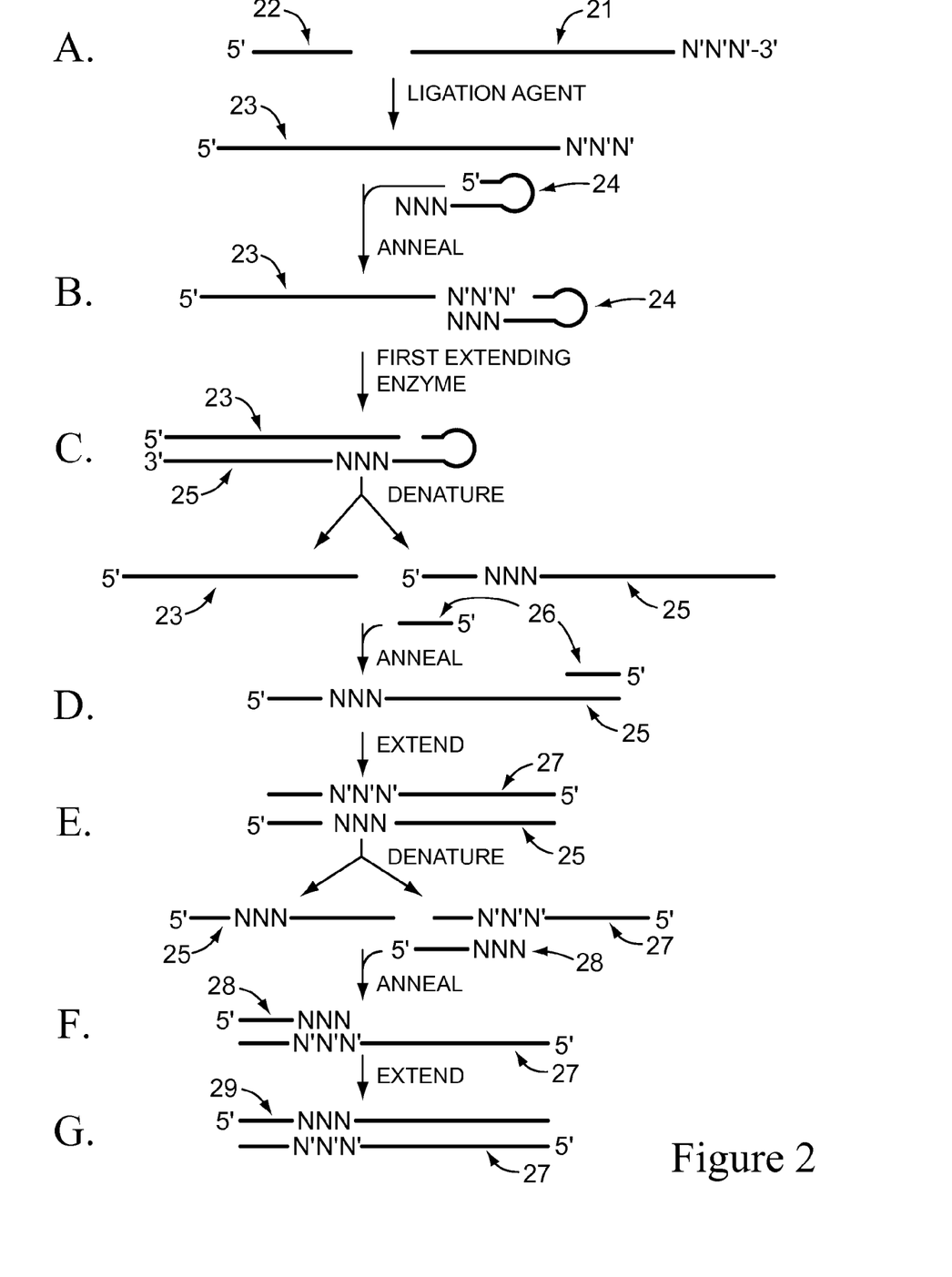
FIG. 2: depicts an illustrative embodiment of certain disclosed methods comprising stem-loop reverse primers and single adapter-modified molecules.

The second amplification composition is subjected to denaturing conditions to separate at least some of the multiplicity of different first extension product (25) from their corresponding single adapter-modified molecules (23). At least some of the first forward primers (26) anneal with at least some of the multiplicity of different first extension products (25), as shown in panel D, and at least some of the annealed first forward primers are extended, generating a multiplicity of duplexes, wherein each duplex comprises a newly-synthesized second extension product (27) and the corresponding first extension product (25), as shown in panel E. The second amplification composition is subjected to denaturing conditions to separate at least some of the multiplicity of different second extension products (27) from the corresponding first extension products (25). At least some of the multiplicity of different second extension products (27) anneal with the corresponding different second reverse primers (28), as shown in panel F, and at least some of the annealed second reverse primers are extended to generate a multiplicity of duplexes comprising a newly synthesized third extension product (29) annealed with the corresponding second extension product (27), as shown in panel G. Following this second round of normalization, the multiplicity of different second extension product species and the multiplicity of different third extension product species reflects a normalized population in that the relative concentration of at least one original nucleic acid species has been decreased, the relative concentration of at least one other nucleic acid species has been increased, or both.

According to certain methods, the nucleotide sequence of at least part of a normalized nucleic acid is determined and the small nucleic acid species that corresponds to the normalized nucleic acid is identified. In some embodiments, a primer or a pair of primers comprising a restriction enzyme site(s) are incorporated into a normalized nucleic acid during amplification. The resulting extension products, for example but not limited to a duplex comprising two corresponding extension products, can be cut with an appropriate restriction enzyme and inserted into a suitable cloning vector according to any known method. In some embodiments, a concatemer comprising a multiplicity of restriction fragments is generated and inserted into a vector. The recombinant vector comprising the insert is introduced into an appropriate host cell and the vector is cloned and amplified in vivo, typically involving at least one selection step. The amplified vectors are recovered and the sequence of the insert or at least part of the insert is determined using a sequencing technique and the corresponding small nucleic acid species from the original population can be identified.

In some embodiments, a small nucleic acid species is identified by sequencing at least part of an extension product, including without limitation sequencing at least part of both strands of a duplex comprising two corresponding extension products. For example but not as a limitation, consider a normalized population that was generated using a multiplicity of different reverse primers comprising a degenerate sequence consisting of four nucleotides and that at least one round of normalization was directed to the 3'-end of the small nucleic acid species (as incorporated in their surrogates, including those comprising the complementary 3'-end sequences). Assuming that one small nucleic acid species in the original population included a 3'-end with the sequence 5'-aata-3' and that the same 3' adapter was ligated to at least some of the small nucleic acids of this species, the normalized population should include a multiplicity of extension products with a 3'-end comprising the sequence 5'-atta-[universal 3' adapter sequence]-3' (for purposes of this illustration, "Normalized Nucleic Acid X"). Thus a sequencing primer comprising a sequence that is complementary to the incorporated 3' adapter sequence of Normalized Nucleic Acid X and comprises the tetranucleotide 5'-tatt-3' at its 3'-end (for purposes of this illustration, "Sequencing Primer Y"), should selectively hybridize only with Normalized Nucleic Acid X. The unincorporated primers and dNTPs from the amplification step are removed using ExoSAP-IT® reagent, according to the manufacturer's protocol (USB Corporation P-78200A rev 03/10). A cycle sequencing reaction is performed using Sequencing Primer Y, at least part of the degraded amplification composition comprising Normalized Nucleic Acid X, and an appropriate sequencing reaction mix including suitably labeled ddNTPs, for example but not limited to the Big Dye® Terminator v 1.1 or v3.1 Cycle Sequencing Kit (Applied Biosystems Part Nos. 4337449 and 4337454, respectively), according to any suitable protocol, for example but not limited to the BigDye® Terminator v3.1 Cycle Sequencing Kit Protocol (Applied Biosystems Part No. 4337035 Rev. A 09/2002) and using any suitable detection instrument, including without limitation, an ABI PRISM® 377 DNA Sequencer, an Applied Biosystems 3730 DNA Analyzer, an ABI PRISM® 3100 or 3100-Avant Genetic Analyzer, each including appropriate filters, software, and peripherals, as appropriate; or a slab gel electrophoresis apparatus that is appropriate for running a DNA sequencing gel.

It is to be appreciated that since the sequencing primer includes a specific degenerate sequence or the complement of the degenerate sequence at its 3'-end, it should, under appropriate annealing conditions, selectively anneal with extension products corresponding to small nucleic acid species comprising that degenerate sequence or the complement of that degenerate sequence at their 3'-end or 5'end, as appropriate. Thus, a sequencing reaction using a particular sequencing primer should generate a nucleotide sequence that corresponds to a species of small nucleic acid. In the event that more than one small nucleic acid species in the original population comprise the same 3'-end and/or 5'end, as appropriate for the particular sequencing reaction, a mixed sequence may be obtained starting with the nucleotide at which the sequence of the different small nucleic acid species diverge. Those in the art will appreciate that, with the use of additional sequencing primers, the sequences of each of the related nucleic acids being sequenced can be determined and each of the corresponding small nucleic acid species identified. It is to be understood that sequencing can comprise a multiplicity of different sequencing reactions that can, but need not be, performed in parallel or that any number of single-plex sequencing reactions can be performed. Those in the art will appreciate that other sequencing methods can be employed to determine the nucleotide sequence of at least a part of an extension product and by implication, the corresponding small nucleic acid species. In some embodiments, sequencing comprises a tailed primer or a pair of tailed primers comprising a sequence that includes the degenerate sequence and at least part of the adjacent adapter sequence (or the complement of this sequence) that becomes incorporated into an extension product or further amplicon during amplification. In some embodiments, at least part of the tail portion of such incorporated tailed primers (or its complement) can serve as at least part of a binding site for a sequencing primer. In some embodiments, a multiplicity of different sequencing primers are employed to determine the sequence of a multiplicity of different extension products, typically simultaneously or nearly simultaneously. In some embodiments, a sequencing primer comprises a label including without limitation a fluorophore and the deoxyribonucleotides and/or dideoxyribonucleotides being incorporated during the sequencing are not labeled.

Although the disclosed teachings has been described with reference to various applications, methods, and compositions, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A method for normalizing a population of different small nucleic acid species of varying abundance, wherein each small nucleic acid species is less than thirty nucleotides long, the method comprising, ligating a 3' adapter and a 5' adapter, respectively, to the 3' and 5' ends of at least some of the small nucleic acids in the population to form a multiplicity of different double adapter-modified molecules, wherein the adapters comprise a 3' adapter comprising a first primer-binding site, and a 5' adapter comprising a second primer-binding site;

amplifying at least some of the multiplicity of different double adapter-modified molecules with a formulated relative concentration of primers to generate a normalized population, wherein the formulated relative concentration of primers comprises a multiplicity of primer species each comprising different degenerate sequences at their respective 3'-ends and a corresponding universal primer species, wherein at least one of the degenerate sequences comprises one, two, three, four, five, or six nucleotides, wherein the concentration of the universal primer species is at least ten times greater than the concentration of any one of the primer species comprising a degenerate sequence, and wherein the concentration of the universal primer is greater than the total concentration of the multiplicity of primers comprising different degenerate sequences, and wherein the amplifying comprises a polymerase chain reaction.

2. The method of claim 1, wherein the 3' adapter, the 5' adapter, or the 3' adapter and the 5' adapter further comprise a restriction enzyme cleavage site.

3. The method of claim 1, wherein the 5' adapter, the 3' adapter, or the 5' adapter and the 3' adapter comprise deoxyribonucleotides and ribonucleotides, and wherein at least the terminal nucleotide on the 3'-end of the 5' adapter comprises a ribonucleotide, at least the terminal nucleotide on the 5'-end of the 3' adapter comprises a ribonucleotide, or at least the terminal nucleotide on the 3'-end of the 5' adapter comprises a ribonucleotide and at least the terminal nucleotide on the 5'-end of the 3' adapter comprises a ribonucleotide.

4. The method of claim 3, wherein at least the three terminal nucleotides on the 3'-end of the 5' adapter comprise ribonucleotides, at least the three terminal nucleotides on the 5'-end of the 3' adapter comprise ribonucleotides, or at least the three terminal nucleotides on the 3'-end of the 5' adapter and at least the three terminal nucleotides on the 5'-end of the 3' adapter comprise ribonucleotides.

5. The method of claim 1, wherein the population of different small nucleic acids comprises at least two different noncoding RNAs.

6. The method of claim 5, wherein the normalized population comprises at least two different miRNA species.

7. The method of claim 1, further comprising degrading the small nucleic acid.

8. The method of claim 7, wherein the degrading comprises alkaline hydrolysis or RNase treatment.

9. A method for identifying a species of small nucleic acid in a population of different small nucleic acid species of varying abundance, wherein each small nucleic acid species is less than thirty nucleotides long, the method comprising,
    ligating a 3' adapter and a 5' adapter, respectively, to the 3' and 5' ends of at least some of the small nucleic acids in the population to form a multiplicity of different double adapter-modified molecules, wherein the adapters comprise a 3' adapter comprising a first primer-binding site, and a 5' adapter comprising a second primer-binding site;
    amplifying at least some of the multiplicity of different double adapter-modified molecules with a formulated relative concentration of primers to generate a normalized population, wherein the formulated relative concentration of primers comprises a multiplicity of primer species each comprising different degenerate sequences at their respective 3'-ends and a corresponding universal primer species, wherein at least one of the degenerate sequences comprises one, two, three, four, five, or six nucleotides, wherein the concentration of the universal primer species is at least ten times greater than the concentration of any one of the primer species comprising a degenerate sequence, and wherein the concentration of the universal primer is greater than the total concentration of the multiplicity of primers comprising different degenerate sequences, and wherein the amplifying comprises a polymerase chain reaction;
    determining the nucleotide sequence of a normalized nucleic acid; and
    identifying the corresponding small nucleic acid species.

10. The method of claim 9, wherein the 3' adapter, the 5' adapter, or the 3' adapter and the 5' adapter further comprise a restriction enzyme cleavage site.

11. The method of claim 9, wherein the 5' adapter, the 3' adapter, or the 5' adapter and the 3' adapter comprise deoxyribonucleotides and ribonucleotides, and wherein at least the terminal nucleotide on the 3'-end of the 5' adapter comprises a ribonucleotide, at least the terminal nucleotide on the 5'-end of the 3' adapter comprises a ribonucleotide, or at least the terminal nucleotide on the 3'-end of the 5' adapter comprises a ribonucleotide and at least the terminal nucleotide on the 5'-end of the 3' adapter comprises a ribonucleotide.

12. The method of claim 11, wherein at least the three terminal nucleotides on the 3'-end of the 5' adapter comprise ribonucleotides, at least the three terminal nucleotides on the 5'-end of the 3' adapter comprise ribonucleotides, or at least the three terminal nucleotides on the 3'-end of the 5' adapter and at least the three terminal nucleotides on the 5'-end of the 3' adapter comprise ribonucleotides.

13. The method of claim 9, further comprising degrading the small nucleic acid.

14. The method of claim 9, wherein the determining the nucleotide sequence comprises:
    inserting at least a portion of a normalized nucleic acid into a vector;
    amplifying the vector comprising the insert in a host cell; and
    sequencing at least part of the insert of the amplified vector or its complement.

15. The method of claim 14, wherein the sequencing comprises primer extension, sequencing by hybridization, chemical cleavage, or restriction enzyme mapping.

16. The method of claim 9, wherein the determining the nucleotide sequence comprises sequencing at least part of a normalized nucleic acid or its complement.

17. The method of claim 16, wherein the sequencing comprises primer extension, sequencing by hybridization, chemical cleavage, or restriction enzyme mapping.

18. A method for identifying a miRNA species in a population of different small nucleic acid species of varying abundance, wherein each small nucleic acid species is less than thirty nucleotides long, comprising,
    ligating a 3' adapter and a 5' adapter, respectively, to the 3' and 5' ends of at least some of the small nucleic acids in the population to form a multiplicity of different double adapter-modified molecules, wherein the adapters comprise a 3' adapter comprising a first primer-binding site and a restriction enzyme cleavage site, a 5' adapter comprising a second primer-binding site and a restriction enzyme cleavage site, wherein the 5' adapter and the 3' adapter comprise deoxyribonucleotides and ribonucleotides, and wherein at least the terminal nucleotide on the 3'-end of the 5' adapter comprises a ribonucleotide and at least the terminal nucleotide on the 5'-end of the 3' adapter comprises a ribonucleotide;
    amplifying at least some of the multiplicity of different double adapter-modified molecules with a formulated relative concentration of primers to generate a normalized population, wherein the formulated relative concentration of primers comprises a multiplicity of stem-loop primer species each comprising different degenerate sequences at their respective 3'-ends and a corresponding universal primer species, wherein at least one of the degenerate sequences comprises one, two, three, four, five, or six nucleotides, wherein the concentration of the universal primer species is at least ten times greater than the concentration of any one of the stem-loop primer species comprising a degenerate sequence, and wherein the concentration of the universal primer is greater than the total concentration of the multiplicity of stem-loop primers comprising different degenerate sequences, and wherein the amplifying comprises a polymerase chain reaction; and determining the nucleotide sequence of a normalized nucleic acid, wherein the determining comprises: (a) inserting at least a portion of a normalized nucleic acid into a vector; (b) amplifying the vector comprising the insert in a host cell; and (c) sequencing at least part of the insert of the amplified vector or its complement.; and identifying the corresponding miRNA species.

* * * * *